United States Patent
Niishiro et al.

(10) Patent No.: US 11,759,768 B2
(45) Date of Patent: Sep. 19, 2023

(54) POROUS FORMED BODY AND PRODUCTION METHOD THEREOF, α-OLEFIN DIMERIZATION CATALYST AND PRODUCTION METHOD THEREOF, AND METHOD OF PRODUCING α-OLEFIN DIMER

(71) Applicant: MITSUI CHEMICALS, INC., Tokyo (JP)

(72) Inventors: Ryo Niishiro, Funabashi (JP); Jun Kawahara, Nagareyama (JP); Masami Murakami, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 45 days.

(21) Appl. No.: 17/040,848

(22) PCT Filed: Mar. 28, 2019

(86) PCT No.: PCT/JP2019/013740
§ 371 (c)(1),
(2) Date: Sep. 23, 2020

(87) PCT Pub. No.: WO2019/189636
PCT Pub. Date: Oct. 3, 2019

(65) Prior Publication Data
US 2021/0016248 A1    Jan. 21, 2021

(30) Foreign Application Priority Data

Mar. 29, 2018 (JP) ................. 2018-066083

(51) Int. Cl.
| | |
|---|---|
| C07C 2/24 | (2006.01) |
| B01J 23/04 | (2006.01) |
| B01J 27/232 | (2006.01) |
| B01J 35/10 | (2006.01) |
| B01J 21/04 | (2006.01) |
| B01J 37/00 | (2006.01) |
| B01J 37/02 | (2006.01) |
| C07C 11/113 | (2006.01) |
| C07C 2/10 | (2006.01) |
| C07C 2/12 | (2006.01) |
| B01J 35/00 | (2006.01) |

(52) U.S. Cl.
CPC ............. *B01J 23/04* (2013.01); *B01J 21/04* (2013.01); *B01J 27/232* (2013.01); *B01J 35/002* (2013.01); *B01J 35/0006* (2013.01); *B01J 35/10* (2013.01); *B01J 35/1038* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 37/0018* (2013.01); *B01J 37/02* (2013.01); *B01J 37/0201* (2013.01); *C07C 2/10* (2013.01); *C07C 2/12* (2013.01); *C07C 2/24* (2013.01); *C07C 11/113* (2013.01); *C07C 2521/04* (2013.01); *C07C 2523/04* (2013.01)

(58) Field of Classification Search
CPC . B01J 21/04; B01J 23/04; B01J 27/232; B01J 35/002; B01J 35/0006; B01J 35/10; B01J 35/1061; B01J 35/1076; B01J 35/1066; B01J 35/1071; B01J 35/1038; B01J 35/1042; B01J 37/02; B01J 37/0201; B01J 37/0018; C07C 2/10; C07C 2/12; C07C 2/24; C07C 11/113; C07C 2521/04; C07C 2523/04
USPC ........ 502/344, 346, 355, 439, 503; 585/510, 585/511, 516
See application file for complete search history.

(56) References Cited

U.S. PATENT DOCUMENTS

| | | | | | |
|---|---|---|---|---|---|
| 4,544,790 | A | * | 10/1985 | Drake ...................... | B01J 23/78 585/516 |
| 4,609,637 | A | * | 9/1986 | Drake .................... | B01J 27/232 23/313 R |
| 5,081,094 | A | | 1/1992 | Drake | |

FOREIGN PATENT DOCUMENTS

| | | |
|---|---|---|
| EP | 0474087 B1 | 5/1995 |
| JP | 58-114737 A | 7/1983 |
| JP | 3-42043 A | 2/1991 |
| JP | 7-222927 A | 8/1995 |
| JP | 2006-326418 A | 12/2006 |

(Continued)

OTHER PUBLICATIONS

Chen et al. "A mini-review on solid superbase catalysts developed in the past two decades", RSC Advances, 2013, 3, pp. 3799-3814; Cited in Indian Office Action.

(Continued)

*Primary Examiner* — Elizabeth D Wood
(74) *Attorney, Agent, or Firm* — Rankin, Hill & Clark LLP

(57) ABSTRACT

A porous formed body (Y) including a porous formed body (X) that satisfies the following (x-1) to (x-3), and an alkali metal carbonate or an alkali metal bicarbonate, in which a content of the alkali metal carbonate or the alkali metal bicarbonate is in a range of from 1 part by mass to 230 parts by mass, with respect to 100 parts by mass of the porous formed body (X), and a production method thereof, an α-olefin dimerization catalyst and a production method thereof, and a method of producing an α-olefin dimer:
  requirement (x-1): a volume of pores with a pore diameter in a range of from 0.01 µm to 100 µm is from 0.10 mL/g to 1.00 mL/g;
  requirement (x-2): a median pore diameter of pores with a pore diameter in a range of from 0.01 µm to 100 µm is from more than 0.01 µm to 10.0 µm; and
  requirement (x-3): a crushing strength is from 0.7 kgf to 15.0 kgf.

11 Claims, No Drawings

(56) References Cited

FOREIGN PATENT DOCUMENTS

JP          2008-149275 A     7/2008
WO          2015/093378 A1    6/2015

OTHER PUBLICATIONS

Indian Office Action dated Jan. 22, 2021 issued in the corresponding Indian Patent Application No. 202017041409.
Yankov et al., "Process for Production of Pure 4-Methyl-1-pentene", Chem. Eng. Technol. 17, 1994, pp. 354-357; Cited in Specification.
International Search Report (ISR) dated Jun. 18, 2019 filed in PCT/JP2019/013740.
Jin et al., "Synthesis and characterization of a K/K2CO3-based solid superbase as a catalyst in propylene dimerization", Korean J. Chem. Eng., 2016, vol. 34, No. 2, pp. 298-304; Cited in KROA.
Korean Office Action (KROA) dated Dec. 30, 2021 for corresponding Korean Patent Application No. 10-2020-7027739.

\* cited by examiner

POROUS FORMED BODY AND PRODUCTION METHOD THEREOF, α-OLEFIN DIMERIZATION CATALYST AND PRODUCTION METHOD THEREOF, AND METHOD OF PRODUCING α-OLEFIN DIMER

TECHNICAL FIELD

The present invention relates to a porous formed body and the production method thereof, an α-olefin dimerization catalyst and the production method thereof, and a method of producing an α-olefin dimer.

BACKGROUND ART

α-olefin dimers represented by 4-methyl-1-pentene (including α-olefin co-dimers, the same applies hereinafter) have been used as monomers for polyolefin production. Many basic catalysts have been hereto proposed as catalysts for producing a corresponding dimer through α-olefin dimetization reaction (including α-olefin co-dimerization reaction, the same applies hereinafter). In particular, many catalysts have been used in which an alkali metal is supported on a support containing an anhydrous potassium compound as a main component.

For these catalysts, studies for further enhancing catalytic activity and ease of obtaining target substances (hereinafter, also referred to as "selectivity") have been continuously conducted. Further, a higher initial activity does not ensure sufficient catalyst life, and therefore studies for extending the catalyst life have also been continuously conducted.

Moreover, enhancement of catalytic activity, enhancement of selectivity, and improvement of catalyst life have also been advanced by adjusting the physical properties of anhydrous potassium compounds or supports to be used (for example, see Patent Literatures 1 to 6).

Patent Literature 7 discloses a method of producing, as a formed body used for a support of an α-olefin dimerization catalyst, a porous formed body having a volume of pores which has been adjusted to a specific range. Patent Literature 7 discloses that use of the formed body for a support of the α-olefin dimerization catalyst yields a higher reaction selectivity than those of publicly known catalysts.

Further, Patent Literature 8 discloses that potassium carbonate and a mixture of silica and alumina are used as a support of an α-olefin dimerization catalyst. Non-Patent Literature 1 discloses that a substance obtained by coating the surface of zeolite with potassium carbonate is used as a support of an α-olefin dimerization catalyst.

Patent Literature 1: Japanese Patent Application Laid-Open (JP-A) No. S58-114737
Patent Literature 2: Japanese Patent Application Laid-Open (JP-A) No. H03-42043
Patent Literature 3: Japanese Patent Application Laid-Open (JP-A) No. H07-222927
Patent Literature 4: Japanese Patent Application Laid-Open (JP-A) No. 2006-326418
Patent Literature 5: Japanese Patent Application Laid-Open (JP-A) No. 2008-149275
Patent Literature 6: US Patent Publication (US-B) U.S. Pat. No. 5,081,094 Specification
Patent Literature 7: International Patent Publication (WO-A) No. 2015/093378
Patent Literature 8: European Patent Publication (EU-B) No. 474087 Specification
Non-Patent Literature 1: Chem. Eng. Technol. vol. 17 1994 354

SUMMARY OF INVENTION

Technical Problem

The present inventors conducted various types of studies on catalysts represented by these Patent Literatures. As a result, it is found that the catalysts disclosed in Patent Literatures 1 to 5 exhibit a certain extent of improvement effects such as enhancing catalytic activity or improving selectivity, but the catalyst support is broken (hereinafter, referred to as "powdering" in some cases) in reactions for a long period of time, as a result of which continuous operation tends to be difficult. The present inventors found that, in an aspect in which a reaction in a liquid phase is required, in particular, such as a case of obtaining 3-methyl-1-pentene from ethylene and 1-butene, there is a possibility that a tendency of powdering of the catalyst support is high.

The catalyst prepared by using a support containing potassium bicarbonate disclosed in Patent Literature 6 was not suitable for industrial production due to its powder form. Further, Patent Literature 6 discloses that the support may be formed into pellets or the like, but it is presumed that water used for formation causes dissolution of potassium bicarbonate and precludes smooth filling in a forming die, resulting in nonuniform physical properties of the formed body.

More desirably, the size of pores can be adjusted in the production of the porous formed body. More specifically, a porous formed body having a pore size greater than that of the porous formed body obtained by the method described in Patent Literature 7 may be demanded. Further, as a preferred requirement, it is conceived that a production method in which the shape can be easily controlled is employed.

Patent Literature 8 and Non-Patent Literature 1 do not describe the formed body prepared by using the mixture or substance, and therefore it is difficult to approve their industrial usefulness.

Thus, an embodiment according to the present disclosure is to provide a porous formed body having an excellent powdering suppressing performance in an α-olefin dimerization reaction.

Further, an embodiment according to the disclosure is to provide a method of producing a porous formed body having an excellent powdering suppressing performance in an α-olefin dimerization reaction, an α-olefin dimerization catalyst prepared by using the porous formed body and the production method thereof, and a method of producing an α-olefin dimer prepared by using the catalyst.

Solution to Problem

The disclosure comprises the following embodiments.
<1> A porous formed body (Y), including:
a porous formed body (X) that satisfies the following requirements (x-1) (x-3); and
an alkali metal carbonate or an alkali metal bicarbonate,
wherein a content of the alkali metal carbonate or the alkali metal bicarbonate is in a range of from 1 part by mass to 230 parts by mass, with respect to 100 parts by mass of the porous formed body (X):
requirement (x-1): a volume of pores with a pore diameter in a range of from 0.01 μm to 100 μm is from 0.10 mL/g to 1.00 mL/g;

requirement (x-2): a median pore diameter of pores with a pore diameter in a range of from 0.01 μm to 100 μm is from more than 0.01 μm to 10.0 μm; and requirement (x-3): a crushing strength is from 0.7 kgf to 15.0 kgf.

<2> The porous formed body (Y) according to <1>, wherein the porous formed body (X) further satisfies the following requirement (x-4):

requirement (x-4): the porous formed body (X) contains at least one compound selected from the group consisting of an oxide of a metal or a rare earth element and a complex oxide thereof, zeolite, activated carbon, and SiC.

<3> The porous formed body (Y) according to <1> or <2>, wherein the alkali metal carbonate or the alkali metal bicarbonate is at least one compound selected from the group consisting of $Na_2CO_3$, $NaHCO_3$, $K_2CO_3$, and $KHCO_3$.

<4> The porous formed body (Y) according to any one of <1> to <3>, wherein the porous formed body (Y) has a volume of pores with a pore diameter in a range of from 0.01 μm to 100 μm of from 0.10 mL/g to 0.80 mL/g.

<5> The porous formed body (Y) according to any one of <1> to <4>, wherein the porous formed body (X) is a formed body of $Al_2O_3$.

<6> An α-olefin dimerization catalyst, comprising an alkali metal (D) supported on the porous formed body (Y) according to any one of <1> to <5>.

<7> A method of producing an α-olefin dimerization catalyst, the method comprising a step of supporting an alkali metal (D) on the porous formed body (Y) according to any one of <1> to <5> to obtain an α-olefin dimerization catalyst.

<8> A method of producing an α-olefin dimer, the method comprising a step of performing an α-olefin dimerization reaction in the presence of the α-olefin dimerization catalyst according to <6> to obtain an α-olefin dimer.

<9> A method of producing a porous formed body (Y), the method comprising:

a step of supporting an alkali metal carbonate or an alkali metal bicarbonate on a porous formed body (X) that satisfies the following requirements (x-1) to (x-3), in a range of from 1 part by mass to 230 parts by mass of the alkali metal carbonate or the alkali metal bicarbonate with respect to 100 parts by mass of the porous formed body (X), thereby obtaining a supported material; and a step of heat treating the supported material at 100° C. to 500° C. to obtain a porous formed body (Y):

requirement (x-1): a volume of pores with a pore diameter in a range of from 0.01 μm to 100 μm is from 0.10 mL/g to 1.00 mL/g;

requirement (x-2): a median pore diameter of pores with a pore diameter in a range of from 0.01 μm to 100 μm is from more than 0.01 μm to 10.0 μm; and requirement (x-3): a crushing strength is from 0.7 kgf to 15.0 kgf.

<10> A method of producing the porous formed body (Y) according to <9>, wherein the porous formed body (X) further satisfies the following requirement (x-4):

requirement (x-4): the porous formed body (X) contains at least one compound selected from the group consisting of an oxide and a complex oxide of a metal or a rare earth element, zeolite, activated carbon, and SiC.

<11> The method of producing a porous formed body (Y) according to <9> or <10>, wherein the alkali metal carbonate or the alkali metal bicarbonate is at least one compound selected from the group consisting of $Na_2CO_3$, $K_2CO_3$, $K_2CO_3$, and $KHCO_3$.

<12> The method of producing a porous formed body (Y) according to any one of <9> to <11>, wherein the porous formed body (X) is a formed body of $Al_2O_3$.

<13> The method of producing a porous formed body (Y) according to any one of <9> to <12>, wherein the step of obtaining a supported material comprises supporting by an impregnation method.

Advantageous Effects of Invention

Thus, according to an embodiment according to the present disclosure, provided is a porous formed body having an excellent powdering suppressing performance in an α-olefin dimerization reaction.

Further, according to an embodiment according to the disclosure, provided are a method of producing a porous formed body having an excellent powdering suppressing performance in an α-olefin dimerization reaction, an α-olefin dimerization catalyst prepared by using the porous formed body and the production method thereof, and a method of producing an α-olefin dimer prepared by using the catalyst.

DESCRIPTION OF EMBODIMENTS

The numerical ranges indicated with the use of the term "to" in the present specification indicate ranges including the numerical values before and after the term "to" respectively as the minimum value and the maximum value. In numerical value ranges described in the present specification in a stepwise manner, an upper limit value or a lower limit value described in one numerical value range may be replaced with an upper limit value or a lower limit value of a numerical value range of other stepwise description. In addition, in the numerical value ranges described in the present specification, an upper limit value or a lower limit value of the numerical value range may be replaced with values shown in examples.

In the present specification, a combination of preferable embodiments is a more preferable embodiment.

Note that the unit [kgf] of the crushing strength in the present specification can be converted into [N] by the equation 1 kgf=9.8N.

The term "step" in the present specification encompasses therein not only independent steps, but also more steps as long as desired actions of the steps are achieved even when the steps are not able to be clearly distinguished from the other steps.

<<Porous Formed Body (Y)>>

A porous formed body (Y) according to the disclosure comprises: a porous formed body (X) that satisfies the following requirements (x-1) to (x-3); and an alkali metal carbonate or an alkali metal bicarbonate (hereinafter, also referred to as "specific compound"), and the content of the alkali metal carbonate or the alkali metal bicarbonate is in a range of from 1 part by mass to 230 parts by mass, with respect to 100 parts by mass of the porous formed body (X).

The porous formed body (Y) according to the disclosure has the above-described configuration, and thus exhibits an excellent powdering suppressing performance in an α-olefin dimerization reaction (hereinafter, also referred to as "having an excellent powdering suppressing performance"). That is, having an excellent powdering suppressing performance means that the porous formed body (Y) is difficult to be powderized even in a case of being used for an α-olefin dimerization reaction.

The reason for this not clear, but is presumed as follows. Note that the disclosure is not limited by the following reasons.

The present inventors conducted studies and found that, in a porous formed body (Y) comprising a porous formed body (X) that satisfies requirements (x-1) to (x-3), and a specific compound, in which the content of the specific compound with respect to the porous formed body (X) is in a specific range, the porous formed body (X) serving as a core and the specific compound are combined, and thereby the porous formed body (Y) is difficult to be powderized during a reaction even in a case in which an α-olefin dimerization reaction is performed using the porous formed body (Y) according to the disclosure.

The porous formed body (X) comprised in the porous formed body (Y) according to the disclosure satisfies the requirements (x-1) to (x-3), and contains, for example, a specific metal oxide. The component of the metal oxide is considered to be not only a component having excellent strength, but also a component having substantially no function related to the reaction as a catalyst. Thus, the component may hardly be susceptible to an influence on the structure (for example, difficulty in deformation, and difficulty in break) through the catalytic reaction. Thus, the porous formed body (Y) according to the disclosure is presumably difficult to be powderized more than before, in particular, in the α-olefin co-dimerization reaction.

Further, in a case in which an ordinary Na-supported potassium carbonate catalyst is used for the α-olefin dimerization reaction, the catalyst is presumably powderized due to progression of the dimerization reaction inside the catalyst.

On the contrary, since the porous formed body (Y) according to the disclosure has the above-described configuration, in a case in which an alkali metal (D)-supported material of porous formed body (Y) described later (α-olefin dimerization catalyst) is used for an α-olefin dimerization reaction, reaction points are difficult to be formed inside the porous formed body (Y). Thus, the present inventors consider that the porous formed body (Y) according to the disclosure also has an excellent powdering suppressing performance.

Further, the method of producing the porous formed body (Y) according to the disclosure, having the above-described steps, allows the specific compound to be easily supported on the porous formed body (X) and also yields a structure in which the specific compound is firmly adhered to the porous formed body (X). Thus, it is presumed that, powdering of the resulting porous formed body (Y) is suppressed during the α-olefin dimerization reaction compared to ordinary porous formed bodies produced by compressing the specific compound into tablets, using graphite or the like as a lubricant.

Hereinafter, respective components constituting the porous formed body (Y) according to the disclosure, and the porous formed body (X) and the specific compound that are used for the method of producing the porous formed body (Y) according to the disclosure will be described.

<Porous Formed Body (X)>

The porous formed body (Y) according to the disclosure contains a porous formed body (X) that satisfies the following requirements (x-1) to (x-3) (hereinafter also simply referred to as "porous formed body (X)"):

requirement (x-1): a volume of pores with a pore diameter in a range of from 0.01 μm to 100 μm is from 0.10 mL/g to 1.00 mL/g;

requirement (x-2): a median pore diameter of pores with a pore diameter in a range of from 0.01 μm to 100 μm is from more than 0.01 μm to 10.0 μm; and requirement (x-3): a crushing strength is from 0.7 kgf to 15.0 kgf.

From the perspective of suppressing powdering, the porous formed body (Y) according to the disclosure is preferably a supported material in which a specific compound described later is supported on the porous formed body (X) that satisfies requirements (x-1) to (x-3) and serves as a support. The supported material is difficult to be powderized even in a case of using the porous formed body (Y) in the α-olefin dimerization reaction.

Hereinafter, the respective requirements that the porous formed body (X) satisfies will be described.

(x-1) Volume of Pores

The volume of pores of the porous formed body (X) with a pore diameter (hereinafter, also simply referred to as "pore diameter (X)") in a range of from 0.01 μm to 100 μm (hereinafter, also simply referred to as "volume of pores (X)") is from 0.10 mL/g to 1.00 mL/g, preferably from 0.20 mL/g to 0.80 mL/g, and more preferably from 0.26 mL/g to 0.77 mL/g from the perspective of enhancing reaction selectivity when the resulting porous formed body (Y) is applied to a support of an α-olefin dimerization catalyst.

Note that, in the present specification, the term "volume of pores" refers to the total volumes of all pores with a pore diameter (X) in a range of from 0.01 μm to 100 μm.

The volume of pores (X) can be adjusted according to, for example, the type of the raw material of the porous formed body to be used, and a formation method or condition.

The volume of pores (X) and the pore diameter (X) can be determined by the pore distribution measured by mercury porosimetry. Note that, in the present specification, the volume of pores means, unless otherwise noted, the value of volume of pores with a pore diameter (X) (hereinafter, also referred to as "pore size (X)") in a range of from 0.01 μm to 100 μm.

In the measurement method of the volume of pores in the disclosure, the relationship of each pore size and volume of pores can be determined by performing measurement at 50 points to 100 points in a pressure range of 1.0 psi (6894.76 Pa) to 33,000 psi (2275.27× $10^3$ Pa) using an Auto Pore IV) (model), available from Micromeritics Instrument Corp. to measure the amount of mercury intruded into pores.

The measurement method is based on the principle in which the pore size, into which mercury is intruded, is determined from the pressure of mercury through characteristics of mercury. The volume of pores with a pore diameter in a range described later is determined from the measurements of the pore size and the volume of pores that have been similarly measured.

(x-2) Median Pore Diameter

The median pore diameter of pores of the porous formed body (X) with a pore diameter (X) in a range of from 0.01 μm to 100 μm is from more than 0.01 μm to 10.0 μm, and preferably from 0.10 μm to 10.0 μm from the perspective of enhancing reaction selectivity when the resulting porous formed body (Y) is applied to a support of an α-olefin dimerization catalyst.

In the present specification, the median pore diameter (X) refers to the pore size in which, when the pore diameters (X) (pore sizes (X)) in a range of from 0.01 μm to 100 μm are measured by mercury porosimetry, and the pore sizes in this range are divided into two groups based on the cumulative 50% pore size, the number of pore sizes of a larger group (larger size side) and the number of pore sizes of a smaller group (smaller size side) are the same.

The measurement method of the median pore diameter (X) is described in the section of Examples.

(x-3) Crushing Strength

The crushing strength of the porous formed body (X) is from 0.7 kgf to 15.0 kgf, preferably 1.0 kgf or more, and more preferably 1.5 kgf or more.

Here, the crushing strength refers to the strength in the radial direction of the porous formed body.

Examples of the shape of the porous formed body (X) are, but are not particularly limited, a tablet shape, a noodle shape, a columnar shape (pellet shape), a convex shape, a ring shape, and a spherical shape. For any of the shapes, the direction corresponding to the radial direction exists. In the case of a porous formed body having a shape with no direction corresponding to the radial direction, the strength at the weakest direction is defined as the crushing strength.

Note that the crushing strength is generally known as a physical property that represents the pressure resistance strength of granules. The crushing strength is usually determined by pressurizing one formed body having a shape such as a pellet shape or a tablet shape in the barrel direction (major axis direction) and measuring the force at crushing.

There is described a test method in HS Z8841(1993) "Granules and agglomerates-Test methods for strength".

(x-4) Composition

The porous formed body (X) preferably contains at least one compound selected from the group consisting of an oxide of a metal or a rare earth element (hereinafter, also simply referred to as "oxide") and a complex oxide thereof (hereinafter, simply referred to as "complex oxide"), zeolite, activated carbon, and SiC.

The compound may be used singly, or in combination of two or more types thereof.

Examples of the metal comprise Al, Si, Ti, Zr, Ca, Sr, Ba, Na, K, Cs, V, Cr, Mn, Fe, Co, Ni, Cu, Zn, Nb, Mo, Ru, Rh, Pd, Ag, Cd, W, Ir, Pt, and Au.

Examples of the rare earth element comprise scandium (Sc), yttrium (Y), and lanthanoid.

From the perspective of preparation of the porous formed body (Y) and use as the α-olefin dimerization catalyst, the porous formed body (X) preferably contains an oxide and a complex oxide of a metal, more preferably contains an oxide and a complex oxide of Al, Si, Ti, Zr, Mn, Co, Ni, Cu, Zn, Mo, W, Ca, Sr, Ba, Na, K or Cs, still more preferably contains an oxide of Al, Si, Ti or Zr, and particularly preferably contains $Al_2O_3$. The porous formed body (X) is particularly preferably an $Al_2O_3$ formed body.

Note that the oxide, complex oxide, zeolite, activated carbon, or SiC contained in the porous formed body (Y) can be confirmed by, for example, the following method. The porous formed body (Y) is impregnated with water to dissolve and thus remove the specific compound supported, followed by drying. Then, the dried resultant is identified by X-ray diffraction (XRD), X-ray fluorescence analysis (XRF), or high frequency inductive-coupling plasma (ICP) emission analysis. The pore shape or the like can also be measured by utilizing mercury porosimetry.

The content of at least one compound selected from the group consisting of the oxide, complex oxide, zeolite, activated carbon, and SiC is preferably in a range of from 70% by mass to 100% by mass, and more preferably in a range of from 80% by mass to 100% by mass with respect to the total mass of the porous formed body (X).

The size and shape of the porous formed body (X) is not particularly limited. The shape of the porous formed body (X) can be selected according to the conditions of a forming apparatus or the like. The shape may be any of a tablet shape, a noodle shape, a columnar shape (pellet shape), a convex shape, a ring shape, and a spherical shape.

A commercially available forming apparatus can be used for the forming apparatus used for forming the porous formed body (X), and an apparatus in a suitable scale can be appropriately selected according to the production amount.

In a case in which the shape of the porous formed body (X) is, for example, a columnar shape, the porous formed body (X) can usually be formed with a diameter of from 2 mm to 5 mm and a height of 2 mm to 7 mm.

In a case in which a porous formed body (X) having a columnar shape and having a size within the above-described range is heat treated and then, for example, applied to a support of the α-olefin dimerization catalyst, diffusion of the raw material and reaction product within the α-olefin dimerization reaction system tends to becomes favorable, resulting in enhanced reaction activity and reaction selectivity in the α-olefin dimerization reaction.

The porous formed body (X) that satisfies the requirements (x-1) to (x-2) can be prepared by using a publicly known method. For example, the porous formed body (X) may be prepared by a method involving heat treating the metal oxide described above or the like in a specific temperature range to cause crystal transition, thereby forming an uneven surface of the porous formed body (X) through change in density. Further, the porous formed body (X) can be controlled to various types of shapes and sizes by using a similar method.

Moreover, it is conceived that this heat treatment activates a functional group structure of acid sites (may also be referred to as "active sites") or the like on the surface of the porous formed body (X), thereby allowing the porous formed body (X) to easily support the specific compound described later firmly. The heat treatment is preferred form this point of view. Further, for the surface of the heat treated porous formed body (X), the specific surface area is large in many cases. This is also considered to be one of the reasons that the specific compound is easily supported on the porous formed body (X) firmly.

The shape of the porous formed body (X) may be formed before the specific compound is supported, or may be formed while the specific compound is supported on the porous formed body (X). The porous formed body (X) is preferably formed before the specific compound is supported, from the perspective of firmly supporting the specific compound. On the other hand, in a case in which the shape of the porous formed body (X) is formed while the specific compound is supported on the porous formed body (X), it is preferable to ensure, in advance, conditions that a desired shape can be formed with the porous formed body (X) alone.

The temperature range for heat treatment is preferably from 1,000° C. to 1,300° C. The lower limit of the temperature range is more preferably 1,050° C., and still more preferably 1,100° C.

The temperature range described above is preferable from the perspective of activation of the acid sites, and formation and maintenance of the porous structure.

Commercially available products may also be used for the porous formed body (X), and examples of the commercially available product are Alumina SA5102, SA3132, and SA31132 (product number). These products are available from Saint-Gobain K.K.

<Specific Compound>

The porous formed body (Y) according to the disclosure contains an alkali metal carbonate or an alkali metal bicarbonate (specific compound).

The porous formed body (Y) containing the specific compound is superior in a powdering suppressing performance in the α-olefin dimerization reaction.

The specific compound is preferably a supported material supported on the porous formed body (X) as a support from the perspective of suppressing powdering.

For example, the specific compound is preferably at least one compound selected from the group consisting of $Na_2CO_3$, $NaHCO_3$, $K_2CO_3$, and $KHCO_3$, more preferably at least one compound selected from the group consisting of $K_2CO_3$ and $Na_2CO_3$, and still more preferably $K_2CO_3$, from the perspective of thermal stability.

The specific compound may be used singly, or in combination of two or more types thereof.

The content of the specific compound is in a range of from 1 part by mass to 230 parts by mass with respect to 100 parts by mass of the porous formed body (X).

When the content of the specific compound is within the range, sufficient catalytic performance can be exerted in a case in which the porous formed body (Y) according to the disclosure is used as an α-olefin dimerization catalyst.

From the point of view, the content of the specific compound is preferably in a range of from 3 parts by mass to 150 parts by mass, more preferably from 5 parts by mass to 100 parts by mass, and still more preferably from 10 parts by mass to 50 parts by mass with respect to 100 parts by mass of the porous formed body (X).

(y-1) Volume of Pores

The volume of pores of the porous formed body (Y) (hereinafter, also simply referred to as "volume of pores (Y)") is preferably from 0.10 mL/g to 0.80 mL/g, and more preferably 0.15 mL/g to 0.80 mL/g from the perspective of enhancing reaction selectivity when the porous formed body (Y) is applied to a support of an α-olefin dimerization catalyst.

The volume of pores (Y) can be adjusted by changing, for example, the amount of the specific compound to be supported, or a supporting method and a supporting condition.

Note that the volume of pores (Y) and the pore diameter (pore size) (hereinafter, also referred to as "pore diameter (Y) (pore size (Y))") are determined by the pore distribution measured by mercury porosimetry. The volume of pores (Y) refers to the value of volume of pores with a pore diameter (Y) (pore size (Y)) in a range of from 0.01 μm to 100 μm. The measurement method of the volume of pores (Y) is described in the section of Examples.

(y-2) Median Pore Diameter

The median pore diameter of the porous formed body (Y) (hereinafter, also simply referred to as "median pore diameter (Y)") is preferably greater than 0.01 μm, and more preferably 0.15 μm or more from the perspective of enhancing reaction selectivity when the porous formed body (Y) is applied to a support of an α-olefin dimerization catalyst. The upper limit of the median pore diameter is preferably 10.0 μm. Note that the median pore diameter (Y) refers to a pore size (D50) in which, when pore diameters (pore sizes) in a range of from 0.01 μm to 100 μm are measured and the pore sizes in this range are divided into two groups based on the cumulative 50% pore size, the number of pore sizes of a larger group (larger size side) and the number of pore sizes of a smaller group (smaller size side) are the same. The measurement method of the median pore diameter (Y) is described in the section of Examples.

(y-3) Crushing Strength

The crushing strength of the porous formed body (Y) is preferably 0.7 kgf or more, more preferably 1.0 kgf or more, and still more preferably 1.5 kgf or more. The upper limit thereof is preferably 15.0 kgf.

Note that the crushing strength of the porous formed body (Y) is synonymous with the crushing strength of the porous formed body (X), and can be determined by a method similar to the method for the porous formed body (X).

The porous formed body (Y) according to the disclosure can be suitably used for a later-described α-olefin dimerization catalyst according to the disclosure.

<<Method of Producing Porous Formed Body (Y)>>

The method of producing the porous formed body (Y) according to the disclosure comprises a step of supporting an alkali metal carbonate or an alkali metal bicarbonate (specific compound) on the porous formed body (X) that satisfies the requirements (x-1) (x-3), in a range of from 1 part by mass to 230 parts by mass of the alkali metal carbonate or the alkali metal bicarbonate, with respect to 100 parts by mass of the porous formed body (X), thereby obtaining a supported material (hereinafter, also referred to as "supporting step"); and a step of heat treating the supported material at 100° C. to 500° C. to obtain a porous formed body (Y) (hereinafter, also referred to as "heat treatment step").

The porous formed body (Y) obtained by the method of producing the porous formed body (Y) according to the disclosure has a structure in which the porous formed body (X) and the specific compound are in firmly adhered. Thus, the resulting porous formed body (Y) is difficult to be powderized even in a case of being used as a catalyst for an α-olefin dimerization reaction. As a result, the α-olefin dimerization reaction can be continued for a long period of time.

The porous formed body (X) and alkali metal carbonate or alkali metal bicarbonate used for the method of producing the porous formed body (Y) according to the disclosure is synonymous with the porous formed body (X) and alkali metal carbonate or alkali metal bicarbonate in the porous formed body (Y) according to the disclosure, and a preferred aspect is the same.

Hereinafter, respective steps of the method of producing the porous formed body (Y) according to the disclosure will be descried.

<Supporting Step>

The supporting step is a step of supporting a specific compound on a porous formed body (X) in a range of from 1 part by mass to 230 parts by mass with respect to 100 parts by mass of the porous formed body (X) to obtain a supported material.

The amount of the specific compound supported on the porous formed body (X) (hereinafter, also referred to as "supported amount") is preferably 2 parts by mass or more, more preferably 5 parts by mass or more, and still more preferably 10 parts by mass or more with respect to 100 parts by mass of the porous formed body (X) from the perspective of obtaining a structure in which the porous formed body (X) and the specific compound firmly adhere to each other. From the similar point of view, the supported amount of the specific compound in the porous formed body (X) is preferably 200 parts by mass or less, more preferably 150 parts by mass or less, still more preferably 100 parts by mass or less, and particularly preferably 50 parts by mass or less with respect to 100 parts by mass of the porous formed body (X).

In the supporting step, the specific compound may be dissolved or dispersed in a solvent, and is preferably dissolved in a solvent and used from the perspective of obtaining a high supporting ratio. The solvent is preferably water.

In a case in which the specific compound is dissolved in water and used, the concentration of the aqueous solution of the specific compound is preferably from 10% by mass to 50% by mass, and more preferably from 30% by mass to 50% by mass from the perspective of obtaining a high supporting ratio.

As the method of supporting the specific compound on the porous formed body (X) (hereinafter, also referred to as "supporting method"), various types of methods can be employed.

Examples of the supporting method comprise a deposition method, a sputtering method, a chemical vapor deposition method (CVD method), and an impregnation method.

The supporting method is preferably an impregnation method from the perspective of dissolving the specific compound in water.

The impregnation method is not particularly limited, and may also be, for example, a method in which the porous formed body (X) is impregnated with an aqueous solution of the specific compound while the aqueous solution is stirred, or may also be a method in which the porous formed body (X) is impregnated while the aqueous solution of the specific compound is allowed to stand without stirring. These methods may also be employed in combination.

In a case in which the supporting step in the method of producing the porous formed body (Y) is a step of supporting the specific compound by the impregnation method to obtain a supported material, the supporting step is preferably a step of impregnating the porous formed body (X) with an aqueous solution of the specific compound that has been adjusted to a predetermined concentration from the perspective of obtaining a high supporting ratio.

In a case in which the porous formed body (X) is impregnated with an aqueous solution of the specific compound while the aqueous solution is allowed to stand, the standing time is preferably 1 hour or longer, more preferably 3 hours or longer, and still more preferably 5 hours or longer from the perspective of sufficiently dispersing the aqueous solution of the specific compound in pores (i.e., surface of the pores) of the porous formed body (X). The upper limit of the standing time is preferably 24 hours from the perspective of production suitability.

From the perspective of obtaining a high supporting ratio, the method of producing the porous formed body (Y) according to the disclosure preferably comprises, in the supporting step, a step of impregnating a porous formed body (X) with a specific compound and then taking out a supported material from an aqueous solution of the specific compound (hereinafter, also referred to as "step of recovering a supported material").

The method of taking out the supported material from the aqueous solution of the specific compound is not particularly limited, and may be, for example, a method in which water is vaporized through evaporation drying, or a method in which the supported material is recovered from the aqueous solution of the specific compound with a sieve. In a case in which the supported material is recovered from the aqueous solution of the specific compound with a sieve, for example, the supported material can be taken out with low energy as well as ease compared to the case of evaporation drying.

<Heat Treatment Step>

A heat treatment step is a step of heat treating the supported material at 100° C. to 500° C. to obtain a porous formed body (Y).

By heat treating the supported material in the temperature range, the supported material can be sufficiently dried. In a case in which the specific compound supported on the supported material is at least one compound selected from the group consisting of $NaHCO_3$ and $KHCO_3$, these compounds are thermally decomposed to generate gas such as water vapor, and thereby a porous formed body (Y) having a volume of pores suitable for a catalyst can be obtained.

The temperature in the heat treatment step is from 100° C. to 500° C., preferably from 150° C. to 450° C., and more preferably from 180° C. to 400° C. under the atmospheric pressure.

The temperature for heat treatment may optionally be set according to the type of specific compound.

As described above, the porous formed body (Y) produced by the production method according to the disclosure excels in strength and uniformity of the shape, and is therefore suitable for a catalyst support, in particular, a support for an α-olefin dimerization catalyst.

Note that the (Y) obtained by the production method according to the disclosure is suitably used as a support for an α-olefin dimerization catalyst, and may also be used as a catalyst support other than the support for an α-olefin dimerization catalyst.

<<α-Olefin Dimerization Catalyst>>

The α-olefin dimerization catalyst according to the disclosure is a catalyst in which an alkali metal (D) is supported on the porous formed body (Y) according to the disclosure. That is, the α-olefin dimerization catalyst according to the disclosure is a supported material of the porous formed body (Y) and an alkali metal (D).

Examples of the alkali metal (D) comprises lithium, sodium, potassium, and the alkali metal (D) is preferably sodium, potassium, or a mixture of sodium and potassium from the perspective of catalytic activity. Here, the alkali metal (D) refers to a zero-valent metal which is not ionized. In a case in which the purity of alkali metal is 90% or more, the alkali metal (D) may contain a component other than alkali metal, but preferably does not substantially contain such a component.

In the disclosure, the term "substantially not containing" refers to the content being less than 1% by mass, and the content is preferably less than 0.1% by mass. The purity of alkali metal refers to the mass fraction of alkali metal in the α-olefin dimerization catalyst.

Examples of the component other than alkali metal comprise various types of oxides or hydroxides of metal elements other than the elements of Group 1 in the periodic table, and metal elements other than the elements of Group 1 in the periodic table.

The alkali metal (D) may be used singly, or in combination of two or more types thereof.

The content of the alkali metal (D) in the α-olefin dimerization catalyst (i.e., the supporting ratio of the alkali metal (D)) is usually in a range of from 0.5% by mass to 15% by mass, and preferably from 1% by mass to 13% by mass per 100% by mass total of the alkali metal (D) and the support (i.e., porous formed body (Y)).

<<Method of Producing a-Olefin Dimerization Catalyst>>

The method of producing the α-olefin dimerization catalyst according to the disclosure comprises a step of supporting an alkali metal (D) on the porous formed body (Y) according to the disclosure to obtain an α-olefin dimerization catalyst.

The method of producing the α-olefin dimerization catalyst according to the disclosure comprises the above-described step, and therefore an α-olefin dimerization catalyst having an excellent powdering suppressing performance can be obtained. Further, the method of producing the α-olefin dimerization catalyst according to the disclosure comprises the above-described step, and therefore an α-olefin dimerization catalyst having excellent reaction selectivity in the α-olefin dimerization reaction can be easily obtained.

In the method of producing the α-olefin dimerization catalyst, the method of supporting the alkali metal (D) on the porous formed body (Y) according to the disclosure may employ various types of publicly known supporting method.

The temperature during the supporting treatment is usually in a range of from 150° C. to 400° C. under the atmospheric pressure. The temperature during the supporting treatment is preferably in a range of from 200° C. to 350° C., and more preferably 200° C. to 300° C. from the perspective of obtaining a catalyst which is excellent in catalytic activity, catalyst life, and selectivity to the α-olefin dimerization product. The atmosphere during the supporting treatment may also be a reducing atmosphere or an inert atmosphere as long as the atmosphere is not a moisture atmosphere or an oxidative atmosphere. In consideration of safety and economic efficiency, the supporting treatment is preferably performed in a nitrogen atmosphere.

To uniformly support the alkali metal (D) during supporting treatment, the alkali metal (D) is preferably supported on the porous formed body (Y) while the porous formed body (Y) and the alkali metal (D) are vibrated, rotated, or stirred.

The alkali metal (D) is known to be brought into contact with a support (porous formed body (Y)) under heating to cause exchange reaction with alkali metal contained in the support.

The method of producing the α-olefin dimerization catalyst preferably further comprises a step of preparing a porous formed body (Y).

Examples of the step of preparing the porous formed body (Y) are various steps shown in the method of producing the porous formed body (Y) descried above, and preferred steps are the same.

The porous formed body (Y) obtained by the method of producing the porous formed body (Y) according to the disclosure is a porous formed body, the pore size of which has been adjusted larger than formed bodies produced in the related art. Further, there is a correlation between the supporting ratio of the alkali metal (D) and catalytic activity, and therefore a porous formed body the pore size of which has been adjusted to larger can support a larger amount of the alkali metal (D). Thus, the α-olefin dimerization catalyst according to the disclosure enables α-olefin dimerization reaction with higher activity.

Note that, in general, there is a tendency that a higher catalytic activity results in a large load on the support, leading to increase in crashing (powdering) of the catalyst support (porous formed body (Y)). However, the strength (e.g., the crushing strength in the radial direction) of the porous formed body (Y) is ensured, and it is therefore conceived that the α-olefin dimerization catalyst is difficult to be crushed (powderized).

In a case in which the surface of the porous formed body (Y) according to the disclosure is observed, there is a case where distinction between the color derived from the porous formed body (X) and the color derived from the specific compound tends to be relatively easy.

The color of surface of the porous formed body (Y) according to the disclosure is generally a black color, which is the color derived from the specific compound. Additionally, for the color of the surface of the porous formed body (Y) according to the disclosure, the proportion of the color derived from the specific compound is preferably high from the perspective of suppressing powdering.

The color of the surface of the porous formed body (Y) according to the disclosure can be evaluated based on an indicator (CI) indicating the proportion of the color derived from the specific compound.

In the present specification, the indicator (CI) indicating the proportion of the color derived from the specific compound (hereinafter, also referred to as "indicator (CI)") can be determined as follows.

As describe above, the specific compound (X) has a substantially particle shape.

1: An image of the porous formed body (Y) is taken by a digital camera by adjusting the magnification of the digital camera so that 50 or more of porous formed bodies (Y) is within the field of view, and then 50 porous formed bodies (Y) are randomly selected from the image.

2: Then, the 50 porous formed bodies (Y) are classified into the following three types: (i) almost all the surface of the porous formed body (Y) have the color derived from the specific compound; (ii) a part of the surface of the porous formed body (Y) has the color; and (iii) almost all the surface of the porous formed body (Y) has no color.

3: The porous formed bodies (Y), which have been classified into (i) to (iii), are respectively scored as follows, and the sum of the scores is taken as the indicator (CI).

2 points: almost the entire surface of the porous formed body (Y) exhibits the color derived from the specific compound.

1 point: the surface of the porous formed body (Y) is partially colored.

0 point: almost all the surface of the porous formed body (Y) is not colored.

Accordingly, in a case in which all of the 50 porous formed bodies (Y) exhibit the color derived from the specific compound, the indicator (CI) is 100 points, and in a case in which almost all the surface of the porous formed body is not colored (i.e., the specific compound is not supported) is 0 point.

The indicator (CI) is preferably 100≥indicator (CI)≥20 from the perspective of suppressing powdering.

The lower limit of the indicator (CI) value is preferably 30, more preferably 40, and still more preferably 45. In contrast, the upper limit of the indicator (CI) value is preferably 95, and more preferably 92.

The (CI) value is preferably from 30 to 95, preferably from 40 to 92, and more preferably from 45 to 92 from the perspective of suppressing powdering.

In a case in which the size of the porous formed body (Y) is small, the indicator (CI) value can be obtained by taking an image with a suitable device such as an optical microscope in place of the digital camera.

<<Method of Producing α-Olefin Dimer>>

The method of producing the α-olefin dimer according to the disclosure comprises a step of performing an α-olefin dimerization reaction in the presence of the α-olefin dimerization catalyst according to the disclosure to obtain an α-olefin dimer.

The method of producing an α-olefin dimer comprises the above-described step and involves an α-olefin dimerization reaction in the presence of an α-olefin dimerization catalyst having an excellent powdering suppressing performance. Thus, excellent selectivity to an α-olefin dimerization product is easily achieved, and an α-olefin dimer can be obtained in a high yield.

Specific examples of the α-olefin used for the method of producing the α-olefin dimer are lower α-olefins such as ethylene, propylene, 1-butene, isobutylene, and 1-pentene.

In the method of producing an α-olefin dimer, by performing an α-olefin dimerization reaction in the presence of the α-olefin dimerization catalyst, 4-methyl-1-pentene through dimerization of propylene and 3-methyl-1-pentene through co-dimerization of 1-butene and ethylene can be obtained in a high yield even in the dimerization reaction of a lower α-olefin.

In the method of producing an α-olefin dimer according to the disclosure, the α-olefin dimerization catalyst having an excellent powdering suppressing performance according to the disclosure is used, and therefore 4-methyl-1-pentene, 3-methyl-1-pentene, or the like can be stably produced in a high yield for a long period of time.

In the method of producing an α-olefin dimer according to the disclosure, the reaction temperature in the α-olefin dimerization reaction is normally from 0° C. to 300° C., and preferably from 50° C. to 200° C.

Further, the reaction pressure is usually normal pressure, that is, in a range of from approximately 0.1 MPa to 19.6 MPa (200 kg/cm$^2$-G), and preferably from 1.96 MPa to 14.7 MPa (20 kg/cm$^2$-G to 150 kg/cm$^2$-G).

The state of α-olefin in the α-olefin dimerization reaction varies depending on conditions of dimerization reaction and the type of α-olefin to be used. The α-olefin can generally assume a liquid phase state, a gas phase state or a supercritical state.

Moreover, the α-olefin dimerization reaction can be performed in a fixed bed system, or in a fluidized bed system. In particular, the α-olefin dimerization reaction can be preferably performed in a fixed bed system. In a case in which dimerization reaction is performed in a fixed bed system, the liquid hourly space velocity (LHSV) of the α-olefin is usually in a range of from 0.1 h$^{-1}$ to 10 hr$^{-1}$, and preferably from 0.5 hr$^{-1}$ to 5 hr$^{-1}$.

Unreacted α-olefins and dimerization reaction products are separated from the mixture after completion of the dimerization reaction according to an ordinary method, and the unreacted α-olefins are circulated and reused for dimerization reactions.

EXAMPLES

Hereinafter, embodiments of the disclosure will be described more specifically through examples, but raw materials, the used amount, proportion, treatment content, treatment procedure, and the like shown in the following examples may be suitably modified as long as it does not depart from the spirit of embodiments of the present disclosure. Accordingly, embodiments of the present disclosure are not particularly limited by these examples.

[Measurement of Volume of Pores (X) and (Y), and Median Pore Diameter (X) and (Y)]

As in the method described above, the volume of pores (mL/g) having a pore diameter (i.e., pore size) in a range of from 0.01 μm to 100 μm was measured using a mercury porosimeter (Auto Pore IV (model), available from Micromeritics Instrument Corp.) by mercury porosimetry. Further, the pore size in the above range was measured, and the median pore diameter (μm) was calculated from the measurement.

[Measurement of Crushing Strength of Porous Formed Body]

The crushing strength (kgf) in the radial direction of the porous formed body (i.e., the barrel direction (longitudinal direction) of the columnar formed body) was measured using a digital hardness meter (model: KHT-40N, available from Fujiwara Scientific Company Co., Ltd.) in accordance with the method described in MS Z8841(1993) "Granules and agglomerates-Test methods for strength".

The principle of measurement of the crushing strength involves placing a columnar formed body to be measured on a sample table at rest, lowering a movable pressurizing surface from the upper part at a constant rate, and pushing the surface onto the columnar formed body to measure the strength when the surface crushes the porous formed body.

Example 1

[Porous Formed Body (X1)]

As a porous formed body (X1), Al$_2$O$_3$, available from Saint-Gobain K.K. (product number; SA 5102, diameter: 3.0 mm, height: 2 mm to 7 mm, volume of pores: 0.26 mL/g, median pore diameter: 1.17 μm, and crushing strength: 9.4 kgf) was used.

[Production of Porous Formed Body (Y1)]

Fifty-seven point five grams of the porous formed body (X1) was impregnated with 100 g of a 30% by mass K$_2$CO$_3$ aqueous solution, and then the resultant was allowed to stand at room temperature (25° C.) for 5 hours. Then, the porous formed body (X1) was taken out from the K$_2$CO$_3$ aqueous solution by using a sieve (aperture size: 710 μm), and then heat treated in an electric furnace in dry air at 300° C. for 2 hours. Thus, a porous formed body (Y1) in which 10 parts by mass of K$_2$CO$_3$ was supported on 100 parts by mass of the porous formed body (X1) was obtained.

Table 1 shows the volume of pores, the median pore diameter, and the crushing strength in the radial direction of the obtained porous formed body (Y1).

[Preparation of α-Olefin Dimerization Catalyst (Z1)]

Ninety-eight point zero parts by mass of the obtained porous formed body (Y1) was dried in a nitrogen gas stream at 300° C. for 2 hours, and then 2.0 parts by mass of sodium was added thereto in a nitrogen atmosphere gas stream. Then, the mixture was stirred at 280° C. for 3.5 hours to prepare an α-olefin dimerization catalyst (Z1).

The deposition of sodium which has been added to the supporting container was not observed, and therefore it was determined that the all the amount of sodium was supported on the porous formed body (Y1). The content of sodium in the α-olefin dimerization catalyst (Z1) at that time (i.e., the supporting ratio of sodium 2.0% by mass.

[Evaluation]

—Powdering Suppressing Performance: Powdering Ratio—

[Dimerization Reaction of Ethylene and 1-Butene]

A synthesis reaction of 3-methyl-1-pentene (hereinafter, abbreviated as "3MP-1") through dimerization reaction of ethylene and 1-butene was performed by charging a tubular reactor (diameter: 18 mm) with 2.5 g of the α-olefin dimerization catalyst (Z1) prepared by the preparation method described above, and continuously feeding a mixed solution of ethylene and 1-butene in a catalyst layer at a reactor internal temperature of 80° C., a reaction pressure of 9.3 MPa, and a flow rate of 7.2 g/h. After the flow reaction was performed for 140 hours, the α-olefin dimerization catalyst (Z1) was taken out from the reactor, and the weight of the catalyst was measured.

Thereafter, all of the α-olefin dimerization catalyst (Z1), which has been taken out, was placed in the upper part of a mesh sieve with an aperture size of 500 μm, and sieved by hand. The powdering ratio of the catalyst was calculated by dividing the mass of powder that has passed through the sieve by the weight of the α-olefin dimerization catalyst (Z1) taken out from the reactor. Table 1 shows the results.

Example 2

[Porous Formed Body (X2)]
As a porous formed body (X2), $Al_2O_3$, available from Saint-Gobain K.K. (product number; SA3132, diameter: 3.0 mm, height: 2 mm to 7 mm, volume of pores: 0.55 mL/g, median pore diameter: 0.87 μm, and crushing strength: 1.5 kgf) was used.

[Production of Porous Formed Body (Y2)]
Thirty point nine grams of the porous formed body (X2) was impregnated with 100 g of a 40% by mass $K_2CO_3$ aqueous solution, and then the resultant was allowed to stand at room temperature for 5 hours. Then, the porous formed body (X2) was taken out from the $K_2CO_3$ aqueous solution by using a sieve (opening size: 710 μm), and then heat treated in an electric furnace in dry air at 300° C. for 2 hours. Thus, a porous formed body (Y2) in which 32 parts by mass of $K_2CO_3$ was supported on 100 parts by mass of the porous formed body (X2) was obtained.

Table 1 shows the volume of pores, the median pore diameter, and the crushing strength in the radial direction of the obtained porous formed body (Y2).

[Preparation of α-Olefin Dimerization Catalyst (Z2)]
Ninety point zero parts by mass of the porous formed body (Y2) was dried in a nitrogen gas stream at 300° C. for 2 hours, and then 10.0 parts by mass of sodium was added thereto in a nitrogen atmosphere gas stream. Then, the mixture was stirred at 280° C. for 3.5 hours to prepare an α-olefin dimerization catalyst (Z2).

The deposition of sodium which has been added to the supporting container was not observed, and therefore it was determined that all the amount of sodium was supported on the porous formed body (Y2). The content of sodium in the α-olefin dimerization catalyst (Z2) at that time (i.e., the supporting ratio of sodium) was 10.0% by mass.

An α-olefin dimerization reaction was performed similarly to Example 1 using the obtained α-olefin dimerization catalyst (Z2) and the resultant was evaluated. Table 1 shows the results.

Example 3

[Porous Formed Body (X3)]
As a porous formed body (X3), $Al_2O_3$, available from Saint-Gobain K.K. (product number; SA31132, diameter: 3.0 mm, height: 2 mm to 7 mm, volume of pores: 0.77 mL/g, median pore diameter: 0.15 μm, and crushing strength: 3.5 kgf) was used.

[Production of Porous Formed Body (Y3)]
Twenty-six point eight grains of the porous formed body (X3) was impregnated with 100 g of a 50% by mass $K_2CO_3$ aqueous solution, and then the resultant was allowed to stand at room temperature for 5 hours. Then, the porous formed body (X3) was taken out from the $K_2CO_3$ aqueous solution by using a sieve, and then heat treated in an electric furnace in dry air at 300° C. for 2 hours, Thus, a porous formed body (Y3) in which 68 parts by mass of $K_2CO_3$ was supported on 100 parts by mass of the porous formed body (X3) was obtained.

Table 1 shows the volume of pores, the median pore diameter, and the crushing strength in the radial direction of the obtained porous formed body (Y3).

[Preparation of α-Olefin Dimerization Catalyst (Z3)]
Ninety six point five parts by mass of the porous formed body (Y3) was dried in a nitrogen gas stream at 300° C. for 2 hours, and then 3.5 parts by mass of sodium was added thereto in a nitrogen atmosphere gas stream. Then, the mixture was stirred at 280° C. for 3.5 hours to prepare an α-olefin dimerization catalyst (Z3).

The deposition of the added sodium to the supporting container was not observed, and therefore it was determined that all the amount of sodium was supported on the porous formed body. The content of sodium in the α-olefin dimerization catalyst (Z3) at that time (i.e., the supporting ratio of sodium) was 3.5% by mass. An α-olefin dimerization reaction was performed similarly to Example 1 using the obtained α-olefin dimerization catalyst (Z3) and the resultant was evaluated. Table 1 shows the results.

Example 4

[Porous Formed Body (X4)]
As a porous formed body (X4), $Al_2O_3$, available from Saint-Gobain K.K. (product number; SA31132, diameter: 3.0 mm, height: 2 mm to 7 mm, volume of pores: 0.77 mL/g, median pore diameter: 0.15 μm, and crushing strength: 3.5 kgf) was used.

[Production of Porous Formed Body (Y4)]
Twenty-six point nine grams of the porous formed body (X4) was impregnated with 100 g of a 30% by mass $K_2CO_3$ aqueous solution, and then the resultant was allowed to stand at room temperature for 5 hours. Then, the porous formed body (X4) was taken out from the $K_2CO_3$ aqueous solution by using a sieve, and then heat treated in an electric furnace in dry air at 300° C. for 2 hours. Thus, a porous formed body (Y4) in which 35 parts by mass of $K_2CO_3$ was supported on 100 parts by mass of the porous formed body (X4) was obtained.

Table 1 shows the volume of pores, the median pore diameter, and the crushing strength in the radial direction of the obtained porous formed body (Y4).

[Preparation of α-Olefin Dimerization Catalyst (Z4)]
Eighty-seven point zero parts by mass of the porous formed body (Y4) was dried in a nitrogen gas stream at 300° C. for 2 hours, and then 13.0 parts by mass of sodium was added thereto in a nitrogen atmosphere gas stream. Then, the mixture was stirred at 280° C. for 3.5 hours to prepare an α-olefin dimerization catalyst (Z4).

The deposition of the added sodium to the supporting container was not observed, and therefore it was determined that all the amount of sodium was supported on the porous formed body. The content of sodium in the α-olefin dimerization catalyst (Z4) at that time (i.e., the supporting ratio of sodium) was 13.0% by mass. An α-olefin dimerization reaction was performed similarly to Example 1 using the obtained α-olefin dimerization catalyst (Z4) and the resultant was evaluated. Table 1 shows the results.

Comparative Example 1

[Preparation of Tableted Formed Body (T1)]
To 100 parts by mass of $K_2CO_3$ (available from AGC Inc., purity: 99%), 0.9 parts by mass of graphite (purity: 98%, median size (d50): 7 μm, and specific surface area measured by the BET method: 150 $m^2/g$) was uniformly mixed. The mixture was subjected to tableting while the compression strength was controlled so that the density of the formed body is 1.7 g/mL, followed by heat treatment in dry air at 300° C. for 2 hours, thereby obtaining a tableted formed body (T1).

Table 1 shows the volume of pores, the median pore diameter, and the crushing strength in the radial direction of the obtained tableted formed body (T1).

[Preparation of α-Olefin Dimerization Catalyst (T1)]

An α-olefin dimerization catalyst (T1) was prepared in a similar manner as in Example 3 except that, in Example 3, a tableted formed body (T1) was used in place of the porous formed body (Y3). Table 1 shows the content of sodium in the α-olefin dimerization catalyst (T1) (i.e., the supporting ratio of sodium).

An α-olefin dimerization reaction was performed similarly to Example 1 using the obtained α-olefin dimerization catalyst (T1) and the resultant was evaluated. Table 1 shows the results.

which 28 parts by mass of $K_2CO_3$ is supported on 100 parts by mass of the porous formed body (X5) was obtained.

[Preparation of α-Olefin Dimerization Catalyst (Z5)]

Eighty-seven point zero parts by mass of the porous formed body (Y5) was dried in a nitrogen gas stream at 300° C. for 2 hours, and then 13.0 parts by mass of sodium was added thereto in a nitrogen atmosphere gas stream. Then, the mixture was stirred at 280° C. for 3.5 hours to prepare an α-olefin dimerization catalyst (Z5).

The deposition of the added sodium to the supporting container was not observed, and therefore it was determined that all the amount of sodium was supported on the porous formed body. The supporting ratio at that time was 13.0% by mass. An α-olefin dimerization reaction was performed similarly to Example 1 using the obtained α-olefin dimerization catalyst (Z5). Table 2 shows the results.

TABLE 1

| | | Example 1 | Example 2 | Example 3 | Example 4 | Comparative Example 1 |
|---|---|---|---|---|---|---|
| Porous formed body(X) | x-4: composition | $Al_2O_3$ | $Al_2O_3$ | $Al_2O_3$ | $Al_2O_3$ | — |
| | x-1: average pore volume (mL/g) | 0.26 | 0.55 | 0.77 | 0.77 | — |
| | x-2: median pore diameter (μm) | 1.17 | 0.87 | 0.15 | 0.15 | — |
| | x-3: crushing strength (kgf) | 9.4 | 1.5 | 3.5 | 3.5 | — |
| Specific compound | | $K_2CO_3$ | $K_2CO_3$ | $K_2CO_3$ | $K_2CO_3$ | $K_2CO_3$ |
| Porous formed body (Y) or tableted formed body (T1) | Average pore volume (mL/g) | 0.19 | 0.33 | 0.31 | 0.50 | 0.17 |
| | Median pore diameter (μm) | 1.35 | 3.62 | 0.33 | 0.39 | 0.46 |
| | Crushing strength (kgf) | 12.1 | 2.0 | 5.2 | 4.6 | 2.5 |
| Supporting ratio: | Na (% by mass) | 2 | 10 | 3.5 | 13 | 3.5 |
| Evaluation | Powdering ratio after dimerization reaction (%) | 0 | 0 | 0 | 0 | 29 |

As shown in Table 1, each of the porous formed bodies (Y) of Examples 1 to 4, which comprises a porous formed body (X) that satisfies the requirements (x-1) to (x-4) and at least one compound selected from the group consisting of $Na_2CO_3$, $NaHCO_3$, $K_2CO_3$, and $KHCO_3$, and in which the content of the compound is in a range of from 1 part by mass to 230 parts by mass with respect to 100 parts by mass of the porous formed body (X), exhibited an excellent powdering suppressing performance in an α-olefin dimerization reaction even in the case of using the porous formed bodies (Y) in the α-olefin dimerization reaction.

On the contrary, in the tabletted formed body (T1) of Comparative Example 1, which does not comprise the porous formed body (X) that satisfies the requirements (x-1) to (x-4), powdering due to an α-olefin dimerization reaction was observed in the case of using the tabletted formed body (T1) for the α-olefin dimerization reaction.

Example 5

[Porous Formed Body (X5)]

As a porous formed body (X5), $Al_2O_3$, available from Saint-Gobain K.K. (product number; SA 31132, diameter: 3.0 mm, height: 2 mm to 7 mm, volume or pores: 0.77 mL/g, median pore diameter: 0.15 μm, and crushing strength: 3.5 kgf) which has been subjected to firing treatment at 1,200° C. for 5 hours (volume of pores: 0.69 mL/g, median pore diameter: 0.52 μm, and crushing strength: 3.7 kgf) was used.

[Production of Porous Formed Body (Y5)]

Three hundred grams of the porous formed body (X5) was impregnated with 500 g of a 30% by mass $K_2CO_3$ aqueous solution, and then the resultant was allowed to stand at room temperature for 5 hours. Then, the porous formed body (X5) was taken out from the $K_2CO_3$ aqueous solution by using a sieve, and then heat treated in an electric furnace in dry air at 300° C. for 2 hours. Thus, a porous formed body (Y5) in Example 6

[Porous Formed Body (X6)]

As a porous formed body (X6), $Al_2O_3$, available from Saint-Gobain K.K. (product number; SA31132, diameter: 3.0 mm, height: 2 mm to 7 mm, volume or pores: 0.77 mL/g, median pore diameter: 0.15 μm, and crushing strength: 3.5 kgf) which has been subjected to firing treatment at 1,200° C. for 5 hours (volume of pores: 0.69 mL/g, median pore diameter: 0.52 μm, and crushing strength: 3.7 kgf) was used.

[Production of Porous Formed Body (Y6)]

Thirty-two point eight grams of the porous formed body (X6) was impregnated with 100 g of a 25% by mass $KCO_3$ aqueous solution, and then the resultant was allowed to stand at room temperature for 5 hours. Then, the porous formed body (X6) was taken out from the $K_2CO_3$ aqueous solution by using a sieve, and then heat treated in an electric furnace in dry air at 300° C. for 2 hours. Thus, a porous formed body (Y6) in which 24 parts by mass of $K_2CO_3$ is supported on 100 parts by mass of the porous formed body (X6) was obtained.

[Preparation of α-Olefin Dimerization Catalyst (Z6)]

Eighty-seven point zero parts by mass of the porous formed body (Y6) was dried in a nitrogen gas stream at 300° C. for 2 hours, and then 13.0 parts by mass of sodium was added thereto in a nitrogen atmosphere gas stream. Then, the mixture was stirred at 280° C. for 3.5 hours to prepare an α-olefin dimerization catalyst (Z6).

The deposition of the added sodium to the supporting container was not observed, and therefore it was determined that all the amount of sodium was supported on the porous formed body. The supporting ratio at that time was 13.0% by mass. An α-olefin dimerization reaction was performed similarly to Example 1 using the obtained α-olefin dimerization catalyst (Z6) and the resultant was evaluated. Table 2 shows the results.

Example 7

[Preparation of α-Olefin Dimerization Catalyst (Z7)]

Eighty-four point zero parts by mass of the porous formed body (Y6) was dried in a nitrogen gas stream at 300° C. for 2 hours, and then 16.0 parts by mass of sodium was added thereto in a nitrogen atmosphere gas stream. Then, the mixture was stirred at 280° C. for 3.5 hours to prepare an α-olefin dimerization catalyst (Z6).

The deposition of the added sodium to the supporting container was not observed, and therefore it was determined that all the amount of sodium was supported on the porous formed body. The supporting ratio at that time was 16.0% by mass. An α-olefin dimerization reaction was performed similarly to Example 1 using the obtained α-olefin dimerization catalyst (Z7) and the resultant was evaluated. Table 2 shows the results.

Example 8

A tubular reactor (diameter: 18 mm) was charged with 3.8 g of the α-olefin dimerization catalyst (Z6) prepared in Example 6, and propylene was continuously fed to a catalyst layer at a reactor internal temperature of 140° C., a reaction pressure of 9.8 MPa, and a propylene flow rate of 4 g/h. Thus, 4-Methyl-1-pentene (hereinafter, abbreviated as "4MP-1") was obtained though the propylene dimerization reaction. A flow reaction was performed and the production of 4MP-1 was confirmed. The α-olefin dimerization catalyst (Z6) was taken out from the reactor, and the weight of the catalyst was measured. Thereafter, all of the α-olefin dimerization catalyst (Z6), which has been taken out, was placed in the upper part of a 500 µm mesh sieve, and sieved by hand. The powdering ratio of the catalyst was calculated by dividing the mass of the powder of catalyst (Z6) that has passed through the sieve by the weight of the catalyst (Z6) taken out from the reactor. The powdering ratio of the α-olefin dimerization catalyst (Z6) was 0%.

—Color Evaluation of Surface of Porous Formed Body (Y)—

For the porous formed bodies (Y6) in Example 5 to Example 8, the indicator (CI) was determined for any 50 porous formed bodies (Y6) obtained according to the above-described method from the photograph taken by a digital camera, on the basis of the above-described method. Table 2 shows the results. Note that the indicator (q) in Example 8 was 98.

TABLE 2

| | | Example 5 | Example 6 | Example 7 | Comparative Example 1 |
|---|---|---|---|---|---|
| Porous formed body (X) | x-4: composition | $Al_2O_3$ | $Al_2O_3$ | $Al_2O_3$ | — |
| | x-1: average pore volume (mL/g) | 0.69 | 0.69 | 0.69 | — |
| | x-2: median pore diameter (µm) | 0.52 | 0.52 | 0.52 | — |
| | x-3: crushing strength (kgf) | 3.7 | 3.7 | 3.7 | — |
| Specific compound | | $K_2CO_3$ | $K_2CO_3$ | $K_2CO_3$ | $K_2CO_3$ |
| Porous formed body (Y) or tabletted formed body (T1) | Average pore volume (mL/g) | 0.46 | 0.44 | 0.44 | 0.17 |
| | Median pore diameter (µm) | 0.59 | 0.69 | 0.69 | 0.46 |
| | Crushing strength (kgf) | 4.2 | 3.3 | 3.3 | 2.5 |
| Supporting ratio: Na (% by mass) | | 13 | 13 | 16 | 3.5 |
| Evaluation | Powdering ratio after dimerization reaction (%) | 0 | 0 | 0 | 29 |
| | Conversion ratio of ethylene (%) | 48 | 53 | 50 | 57 |
| | Selectivity of 3methyl-1-pentene (%) | 64 | 70 | 68 | 80 |
| | Indicator (CI) | 98 | 98 | 98 | — |

Table 2 shows that the porous formed bodies (Y) and the α-olefin dimerization catalysts according to the disclosure in Example 5 to Example 7 each have an excellent powdering suppressing performance.

As described above, the porous formed body (Y) and the production method thereof, the α-olefin dimerization catalyst and the production method thereof, and the method of producing an α-olefin dimer according to the disclosure, excel in a powdering suppressing performance in an α-olefin dimerization reaction.

The entire disclosure of Japanese Patent Application No. 2018-066083 filed on Mar. 29, 2018 is incorporated herein by reference.

All publications, patent applications, and technical standards described in the present specification are incorporated herein by reference to the same extent as if each publication, patent application, or technical standard was specifically and individually indicated to be incorporated by reference.

The invention claimed is:

1. A porous formed body (Y), comprising:
   a porous formed body (X) that satisfies the following requirements (x-1) to (x-4); and
   an alkali metal carbonate or an alkali metal bicarbonate,
   wherein the porous formed body (Y) has a volume of pores with a pore diameter in a range of from 0.01 µm to 100 µm of from 0.15 mL/g to 0.80 mL/g;
   a content of the alkali metal carbonate or the alkali metal bicarbonate is in a range of from 1 part by mass to 230 parts by mass, with respect to 100 parts by mass of the porous formed body (X);
   requirement (x-1): a volume of pores with a pore diameter in a range of from 0.01 µm to 100 µm is from 0.10 mL/g to 1.00 mL/g;
   requirement (x-2): a median pore diameter of pores with a pore diameter in a range of from 0.01 µm to 100 µm is from more than 0.01 µm to 10.0 µm;

requirement (x-3): a crushing strength is from 0.7 kgf to 15.0 kgf; and requirement (x-4): the porous formed body (X) contains at least one compound selected from the group consisting of an oxide of a metal, an oxide of a rare earth element, a complex oxide of a metal and a rare earth element, zeolite, activated carbon, and SiC.

2. The porous formed body (Y) according to claim 1, wherein the alkali metal carbonate or the alkali metal bicarbonate is at least one compound selected from the group consisting of $Na_2CO_3$, $NaHCO_3$, $K_2CO_3$, and $KHCO_3$.

3. The porous formed body (Y) according to claim 1, wherein the porous formed body (X) is a formed body of $Al_2O_3$.

4. An α-olefin dimerization catalyst, comprising an alkali metal (D) supported on the porous formed body (Y) according to claim 1.

5. A method of producing the α-olefin dimerization catalyst of claim 4, the method comprising a step of supporting the alkali metal (D) on the porous formed body (Y) to obtain the α-olefin dimerization catalyst.

6. A method of producing an α-olefin dimer, the method comprising a step of performing an α-olefin dimerization reaction in the presence of the α-olefin dimerization catalyst according to claim 4 to obtain an α-olefin dimer.

7. A method of producing a porous formed body (Y), the method comprising:

a step of supporting an alkali metal carbonate or an alkali metal bicarbonate on a porous formed body (X) that satisfies the following requirements (x-1) to (x-4), in a range of from 1 part by mass to 230 parts by mass of the alkali metal carbonate or the alkali metal bicarbonate with respect to 100 parts by mass of the porous formed body (X), thereby obtaining a supported material; and a step of heat treating the supported material at 100° C. to 500° C. to obtain a porous formed body (Y):

wherein the porous formed body (Y) has a volume of pores with a pore diameter in a range of from 0.01 μm to 100 μm of from 0.15 mL/g to 0.80 mL/g;

requirement (x-1): a volume of pores with a pore diameter in a range of from 0.01 μm to 100 μm is from 0.10 mL/g to 1.00 mL/g;

requirement (x-2): a median pore diameter of pores with a pore diameter in a range of from 0.01 μm to 100 μm is from more than 0.01 μm to 10.0 μm;

requirement (x-3): a crushing strength is from 0.7 kgf to 15.0 kgf; and requirement (x-4): the porous formed body (X) contains at least one compound selected from the group consisting of an oxide of a metal, an oxide of a rare earth element, a complex oxide of a metal and a rare earth element, zeolite, activated carbon, and SiC.

8. The method of producing a porous formed body (Y) according to claim 7, wherein the alkali metal carbonate or the alkali metal bicarbonate is at least one compound selected from the group consisting of $Na_2CO_3$, $NaHCO_3$, $K_2CO_3$, and $KHCO_3$.

9. The method of producing a porous formed body (Y) according to claim 7, wherein the porous formed body (X) is a formed body of $Al_2O_3$.

10. The method of producing a porous formed body (Y) according to claim 7, wherein the step of supporting an alkali metal carbonate or an alkali metal bicarbonate comprises an impregnation method.

11. The method of producing an α-olefin dimer according to claim 6, the α-olefin dimer is 3-methyl-1-pentene obtained through co-dimerization of 1-butene and ethylene.

* * * * *